(12) United States Patent
Zhang et al.

(10) Patent No.: US 10,353,110 B2
(45) Date of Patent: Jul. 16, 2019

(54) METHOD AND DEVICE FOR OPERATING CT-BASED THREE-DIMENSIONAL IMAGE USED FOR SECURITY INSPECTION

(71) Applicants: TSINGHUA UNIVERSITY, Beijing (CN); Nuctech Company Limited, Beijing (CN)

(72) Inventors: Li Zhang, Beijing (CN); Shuo Wang, Beijing (CN); Yunda Sun, Beijing (CN); Qingping Huang, Beijing (CN)

(73) Assignees: TSINGHUA UNIVERSITY, Beijing (CN); Nuctech Company Limited, Beijing (CN)

( * ) Notice: Subject to any disclaimer, the term of this patent is extended or adjusted under 35 U.S.C. 154(b) by 5 days.

(21) Appl. No.: 15/301,060

(22) PCT Filed: Dec. 16, 2015

(86) PCT No.: PCT/CN2015/097604
§ 371 (c)(1),
(2) Date: Sep. 30, 2016

(87) PCT Pub. No.: WO2016/101829
PCT Pub. Date: Jun. 30, 2016

(65) Prior Publication Data
US 2017/0285218 A1 Oct. 5, 2017

(30) Foreign Application Priority Data
Dec. 23, 2014 (CN) .......................... 2014 1 0811903

(51) Int. Cl.
*G01N 23/00* (2006.01)
*G01V 5/00* (2006.01)
(Continued)

(52) U.S. Cl.
CPC ............. *G01V 5/005* (2013.01); *G01N 23/04* (2013.01); *G01N 23/046* (2013.01);
(Continued)

(58) Field of Classification Search
CPC ..................................................... G01N 23/04
See application file for complete search history.

(56) References Cited

U.S. PATENT DOCUMENTS

| | | | |
|---|---|---|---|
| 2006/0140473 A1 | 6/2006 | Brooksby et al. | |
| 2008/0152082 A1 | 6/2008 | Bouchard et al. | |
| 2010/0046704 A1* | 2/2010 | Song .................... | G01N 23/04 378/57 |

FOREIGN PATENT DOCUMENTS

| | | |
|---|---|---|
| CN | 101488233 A | 7/2009 |
| CN | 102095663 A | 6/2011 |

(Continued)

OTHER PUBLICATIONS

Jönsson D. et al., "A Survey of Volumetric Illumination Techniques for Interactive Volume Rendering", Computer Graphics Forum 33(1):27-51 (Oct. 2013).
(Continued)

*Primary Examiner* — Dani Fox
(74) *Attorney, Agent, or Firm* — Scully Scott Murphy & Presser (57) ABSTRACT

The present disclosure provides a method and device for operating a CT-based three-dimensional image used for security inspection. The method includes: providing a CT-based three-dimensional image used for security inspection; accepting a selection of an image of an object in the three-dimensional image; and responding to the selection. The present disclosure has strong practicality, and can provide effective reference information for image judgment in the CT-based security inspection field.

16 Claims, 4 Drawing Sheets

(51) Int. Cl.
*G01N 23/04* (2018.01)
*G06T 7/50* (2017.01)
*G06T 7/90* (2017.01)
*G01N 23/046* (2018.01)
*G06T 7/00* (2017.01)
*G06T 7/40* (2017.01)

(52) U.S. Cl.
CPC .............. *G06T 7/0002* (2013.01); *G06T 7/40* (2013.01); *G06T 7/50* (2017.01); *G06T 7/90* (2017.01); *G06T 2207/10072* (2013.01)

(56) References Cited

FOREIGN PATENT DOCUMENTS

| | | |
|---|---|---|
| CN | 102542598 A | 7/2012 |
| CN | 102901703 A | 1/2013 |
| CN | 103366394 A | 10/2013 |
| CN | 103675931 A | 3/2014 |
| CN | 103901489 A | 7/2014 |
| CN | 103926628 A | 7/2014 |
| CN | 105223212 A | 1/2016 |
| EP | 2 750 077 A2 | 7/2014 |

OTHER PUBLICATIONS

European Extended Supplementary Search Report dated Jul. 24, 2017 received in European Patent Application No. 15 87 1897.3.
Hui L. et al., "Depth Based Ray-Casting Volume Rendering", Computer Applications and Software 25(1)109-210 & 237 (Jan. 2008), together with an English-language abstract.
International Search Report dated Mar. 2, 2016 issued in PCT/CN2015/097604.

* cited by examiner

METHOD AND DEVICE FOR OPERATING CT-BASED THREE-DIMENSIONAL IMAGE USED FOR SECURITY INSPECTION

CROSS-REFERENCE TO RELATED APPLICATIONS

The present application is based upon and claims priority to Chinese Patent Application No. 201410811903.8, filed Dec. 23, 2014, the entire contents of which are incorporated herein by reference.

TECHNICAL FIELD

The present disclosure generally relates to image processing field, and more particularly, to a method and device for operating a CT-based three-dimensional image used for security inspection.

BACKGROUND

A multiple-energy X ray security inspection system refers to a new type of security inspection system developed based on a single-energy X ray security inspection system. The multi-energy X ray security inspection system can provide not only the shapes and contents of the objects under inspection, but also information reflecting the effective atomic numbers of the objects under inspection, so that the system can effectively determine whether the objects under inspection are organics or inorganics and display the objects on a color monitor with different colors. This can help operators to distinguish. Existing X ray security inspection systems provide two-dimensional or three-dimensional stereograms of luggage. Usually, objects in luggage are stacked disorderly, overlapping and obscuring each other, which brings difficulties in recognizing hazardous objects comprehensively, fast and effectively. Existing security inspection devices and methods can mark categories of objects with colors, but this can provide very little assistance. During the scanning procedure, screeners (the persons who judge images) have very little time (for example, 10 seconds) to check every image, and this also brings difficulties to the work of the screeners. Thus, there is an urgent need to provide a method and device for operating a CT-based (Computed Tomography based) three-dimensional image used for security inspection, which are capable of assisting screeners to judge images faster and thereby to increase the speed and accuracy of security inspection.

For obtaining of information about CT-based images, accuracy is preferred in industrial and medical applications, and images are mainly obtained from sectional slices. In the security inspection field, convenience and speed are the most important factors which need to be considered, because the screeners can have only about 10 seconds to check every image during the scanning procedure. Thus, in prior arts, it is still not possible to fast and accurately obtain information of target objects when CT-based security inspection is performed within a short time.

SUMMARY

Technical Problems to be Solved
The present disclosure provides a method and device for operating a CT-based three-dimensional image used for security inspection in order to solve the technical problem in prior arts that it is impossible to fast and accurately obtain information of objects which have been scanned by CT.

Technical Solutions
In order to solve the above technical problem, the present disclosure provides a method for operating a CT-based three-dimensional image used for security inspection, including:
providing a CT-based three-dimensional image used for security inspection;
accepting a selection to select an image of an object in the three-dimensional image; and
responding to the selection.

Further, the accepting the selection to select the image of the object in the three-dimensional image, includes:
accepting a selection to entirely select the image of the object in the three-dimensional image.

Further, the accepting the selection to entirely select the image of the object in the three-dimensional image, includes:
accepting a single-click selection or a frame selection on the image of the object in the three-dimensional image to entirely select the image of the object.

Further, the accepting the selection to select the image of the object in the three-dimensional image, includes:
accepting a local selection to locally select the image of the object in the three-dimensional image.

Further, the accepting the local selection to locally select the image of the object in the three-dimensional image includes:
accepting a double-click selection on the image of the object in the three-dimensional image select a section of the image of the object; or
accepting a local frame selection on the image of the object in the three-dimensional image to select a local region of the image of the object.

Further, the responding to the selection includes:
displaying one or more of the following pieces of information: an image contour and a three-dimensional size of the image of the selected object, a density, an atomic number, a CT number and a substance state of the selected object, and information indicating whether the object is a hazardous object; and/or
if the object is the hazardous object, providing an alert or a notification.

Further, the responding to the selection includes:
displaying one or more the following pieces of information: a size of a local region of the image of the selected object, a density, an atomic number, a CT number and a substance state of the selected object, and information indicating whether the object is a hazardous object; andor
if the object is a hazardous object, providing an alert or a notification.

Further, the providing the CT-based three-dimensional image used for security inspection, includes:
performing three-dimensional volume rendering on a CT-based image used for security inspection, and obtaining position information of surfaces of the object in the three-dimensional image.

Further, the performing the three-dimensional volume rendering on the CT-based image used for security inspection, includes:
casting rays of light along a viewing direction;
performing a volume texture sampling on the CT-based image used for security inspection according to the cast rays of light, and obtain color information; and
performing color combination and outputting a three-dimensional volume rendering result.

Further, the obtaining position information of surfaces of the object in the three-dimensional image, includes:

according to a preset transparency threshold, recording positions where the rays of light firstly hit opaque regions in the CT-based image used for security inspection as surface depths of the image of the object;

calculating gradient values of voxels at the positions as normal direction information of the positions; and while outputting the three-dimensional volume rendering of the CT-based image used for security inspection, recording the surface depths and normal direction information of the image of the object in the three-dimensional image.

Further, the responding to the selection includes:

obtaining size information of the selected part according to the surface depths and the normal direction information;

wherein the obtaining of the size information includes:

calculating a variation value of a normal direction from a starting point to an ending point of the selected part; if the variation value is smaller than a preset angle threshold, querying the surface depths and converting the starting point and the ending point into three-dimensional coordinates, and outputting size measurement values in directions in which measurements are needed after coordinate conversion.

Further, the responding to the selection includes:

obtaining voxel collections for different objects in the CT-based three-dimensional image used for security inspection by dividing;

determining at least one selected object from the voxel collections for different objects based on different preset criteria; and performing statistics on voxel information corresponding to the at least one selected object, and outputting size measurements of the object in a three-dimensional space.

According to another aspect, the present disclosure provides a device for operating a CT-based three-dimensional image used for security inspection, including:

an image providing unit configured to provide a CT-based three-dimensional image used for security inspection;

a selection unit configured to accept a selection to select an image of an object in the three-dimensional image provided by the image providing unit; and a responding unit configured to respond to the selection performed by the selection unit.

Further, the selection unit is configured to accept a selection to entirely select the image of the object in the three-dimensional image provided by the image providing unit.

Further, the selection unit is configured to accept a single-click selection or a frame selection on the image of the object in the three-dimensional image to entirely select the image of the object.

Further, the selection unit is configured to accept a local selection to locally select the image of the object in the three-dimensional image provided by the image providing unit.

Further, the selection unit is configured to:

accept a double-click selection on the image of the object in the three-dimensional image to select a section of the image of the object; or accept a local frame selection on the image of the object in the three-dimensional image to select a local region of the image of the object.

Further, the responding unit is configured to:

display one or more of the following pieces of information: an image contour and a three-dimensional size of the image of the object selected by the selection unit, a density, an atomic number, a CT number and a substance state of the selected object, and information indicating whether the object is a hazardous object; and/or if the object selected by the selection unit is a hazardous object, provide an alert or a notification.

Further, the responding unit is configured to:

display one or more the following pieces of information: a size of a local region of the image of the object selected by the selection unit, a density, an atomic number, a CT number and a substance state of the selected object, and information indicating whether the object is a hazardous object; and/or if the object selected by the selection unit is a hazardous object, providing an alert or a notification.

According to another aspect, there is provided a device for operating a CT-based three-dimensional image used for security inspection, including:

A processor; and a memory storing instructions executable by the processor;

wherein the processor is configured to:

provide a CT-based three-dimensional image used for security inspection;

accept a selection to select an image of an object in the three-dimensional image; and respond to the selection.

Advantageous Effects

In the method and device for operating a CT-based three-dimensional image used for security inspection provided by the present disclosure, related information of an object image in a CT-based image can be obtained by performing selection on the CT-based image used for security inspection and responding to the selection. Thus, the present disclosure has strong practicality, and can provide effective reference information for image judgment in the CT-based security inspection field.

BRIEF DESCRIPTION OF THE DRAWINGS

In order to clearly describe embodiments of the present disclosure or technical solutions in prior arts, drawings in connection with embodiments of the present disclosure or technical solutions in prior arts will be described briefly. It is obvious that the drawings described below are some exemplary embodiments of the present disclosure, and one of ordinary skill in this art can conceive other drawings based on these described drawings without creative work.

FIG. 6 is a schematic diagram illustratively showing a starting point and an end point and a length measurement result according to a first embodiment of the present disclosure; in FIG. 6(a), the starting and ending points are on different objects, and in FIG. 6(b), the starting and ending points are on the same object.

DETAILED DESCRIPTION

In order to make objectives, technical solutions and advantages of embodiments of the present disclosure more clear, technical solutions in embodiments of the present disclosure will be described clearly and completely with reference to drawings of embodiments of the present disclosure. It should be noted that the following embodiments are illustrative only, rather than limiting the scope of the disclosure.

Figure 1:
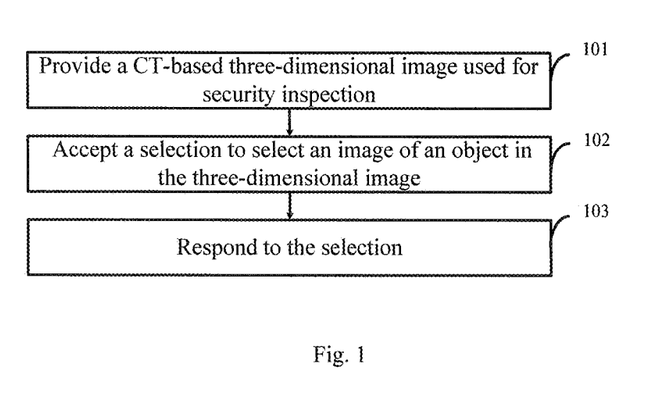
FIG. 1 is a basic flow chart of a method for operating a CT-based three-dimensional image used for security inspection according to an embodiment of the present disclosure.

FIG. 1 is a method for operating a CT-based three-dimensional image used for security inspection according to an embodiment of the present disclosure. As shown in FIG. 1, the method can include the following steps.

In step 101, a CT-based three-dimensional image used for security inspection is provided.

In step 102, a selection to select an image of an object in the three-dimensional image is accepted.

In step 103, responding to the selection is performed.

The selection of the object image in the three-dimensional image can include an entire selection and a local selection. During the entire section, the image of a certain object in the three-dimensional image can be clicked for once or framed to entirely select the image of the object. During operation relating to the local selection, the image of a certain object in the three-dimensional image can be clicked for twice to select one section of the image of the object, that is, a line selection is performed; or, a local frame selection can be performed on the image of a certain object in the three-dimensional image to select a local region of the image of the object, that is, a surface selection is performed.

To respond to the selection, different responses can be performed depending on selection manners of the object image. For example, if the object image is selected entirely, the response procedure can include displaying one or more of the following pieces of information: an image contour and a three-dimensional size of the image of the selected object, a density, an atomic number, a CT number and a substance state of the selected object, and information indicating whether the object is a hazardous object; if the object is the hazardous object, an alert can be provided. If the object image is selected locally, the response procedure can include displaying one or more the following pieces of information: a size of a local region of the image of the selected object, a density, an atomic number, a CT number and a substance state of the selected object, and information indicating whether the object is a hazardous object; and/or if the object is the hazardous object, an alert or a notification is provided.

In above situations, the image contour and the three-dimensional size of the image of the selected object can be realized by separation and selection and measurement of the object image. The density and the atomic number of the object can be obtained by a measurement result of double-energy CT, and the substance state of the object can be determined accordingly, for example, liquid contained in a solid state bottle. According to the above pieces of information, whether the object is a hazardous object can be determined; and if the object is determined as the hazardous object, alerting manners such as flashing lights or whistles can be used to notify the person who judges the image and surrounding travelers or visitors of the danger.

The three-dimensional measurement or length measurement of an object is an important measurement for determining the property of the object, and fast and accurate obtaining of the size information of the object can provide references for determination of the object property. Thus, a quick and accurate three-dimensional rendering and size measurement of a CT-based image is of very important value for assisting image determination.

For a CT-based image, the ray casting algorithm is the most widely used volume rendering method. The method casts a light ray along a fixed direction (usually, a viewing direction) from each pixel in the image, the light rays go through the whole image sequence, and sampling on the image sequence is conducted to obtain color information during the propagation of the light rays, the color values are accumulated according to a light absorption model until the light rays go through the whole image sequence; the resulted color values are the colors for rendering the image. It can be seen that a two-dimensional image can be finally obtained by the ray casting method, and such two-dimensional image cannot restore the depth information of the voxels which the rays cast from pixels pass; the method only records the accumulated colors but does not record relative positional relationships among different objects in the (image) data.

Accordingly, in order to further fast and accurately obtain the size information of the selected object, for example, the providing the CT-based three-dimensional image used for security inspection may further include: performing three-dimensional volume rendering on the CT-based image used for security inspection, and obtaining position information of surfaces of the object in the three-dimensional image. In some specific implementations, the position information may be surface depths of the image of the object and normal direction information. Specifically, the performing the three-dimensional volume rendering on the CT-based image used for security inspection may include: casting rays of light along a viewing direction; performing a volume texture sampling on the CT-based image used for security inspection according to the cast rays of light, and obtain color information; and performing color combination and outputting a three-dimensional volume rendering result. The obtaining of the surface depths of the image of the object and normal direction information may include: according to a preset transparency threshold, recording positions where the rays of light firstly hit opaque regions in the CT-based image used for security inspection, and taking the positions as the surface depths of the image of the object; further, calculating gradient values of voxels at the positions, and taking the gradient values as the normal direction information of the positions; and while outputting the three-dimensional volume rendering of the CT-based image used for security inspection, recording the surface depths and normal direction information of the image of the object in the three-dimensional image.

On this basis, the responding to the selection may include: obtaining size information of the selected part according to the surface depths and the normal direction information. Specifically, the obtaining of the size information may include: calculating a variation value of a normal direction from a starting point to an ending point of the selected part; if the variation value is smaller than a preset angle threshold, querying the surface depths and converting the starting point and the ending point into three-dimensional coordinates, and outputting size measurement values in directions in which measurements are needed after coordinate conversion.

Optionally, the responding to the selection may further include: obtaining voxel collections for different objects in the CT-based three-dimensional image used for security inspection by dividing; determining at least one selected object from the voxel collections for different objects based on different preset criteria; and performing statistics on voxel information corresponding to the at least one selected object, and outputting size measurements of the object in a three-dimensional space. As can be seen from the above descriptions, by the method for measuring the size of the object image provided by the embodiments of the present disclosure, the three-dimensional volume rendering of the CT-based image, the surface depths of the object, and the normal direction information can be obtained simultaneously, and thus three-dimensional coordinate conversion and outputting of measurement results can be performed fast and accurately. The method provided by embodiments of the present disclosure has strong practicality, and can provide effective reference information for image judgment in the CT-based security inspection field.

First Embodiment

Figure 2:
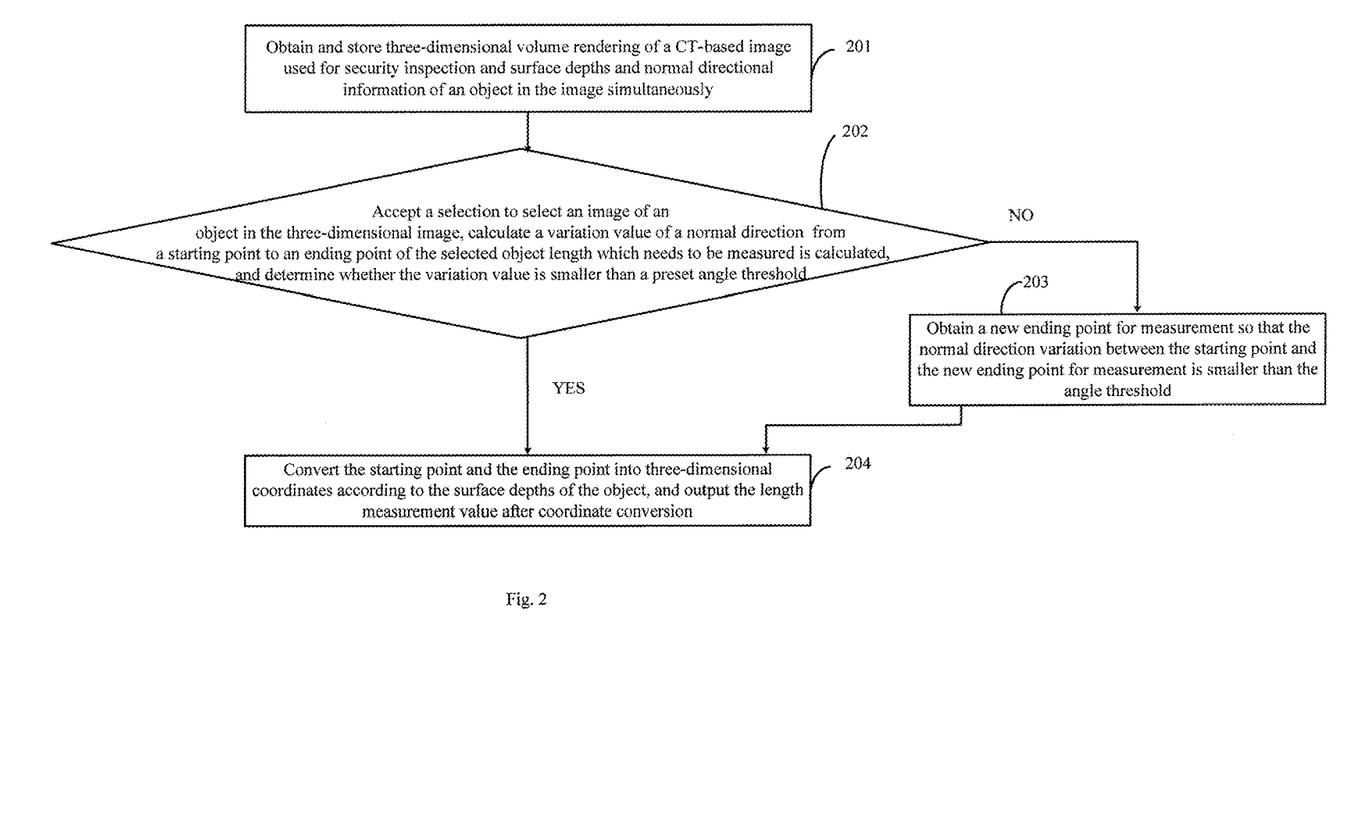
FIG. 2 is a flow chart of a method for operating a CT-based three-dimensional image used for security inspection according to a first embodiment of the present disclosure.

The first embodiment of the present disclosure provides a length measurement method for a CT-based three-dimensional image used for security inspection so as to explain the specific implementation of the present disclosure. As shown in FIG. 2, the method includes the following steps.

In step 201, three-dimensional volume of a CT-based image used for security inspection and surface depths and normal directional information of an object in the image (i.e., DVR, FHP and FHN) are obtained and stored simultaneously.

Figure 3:
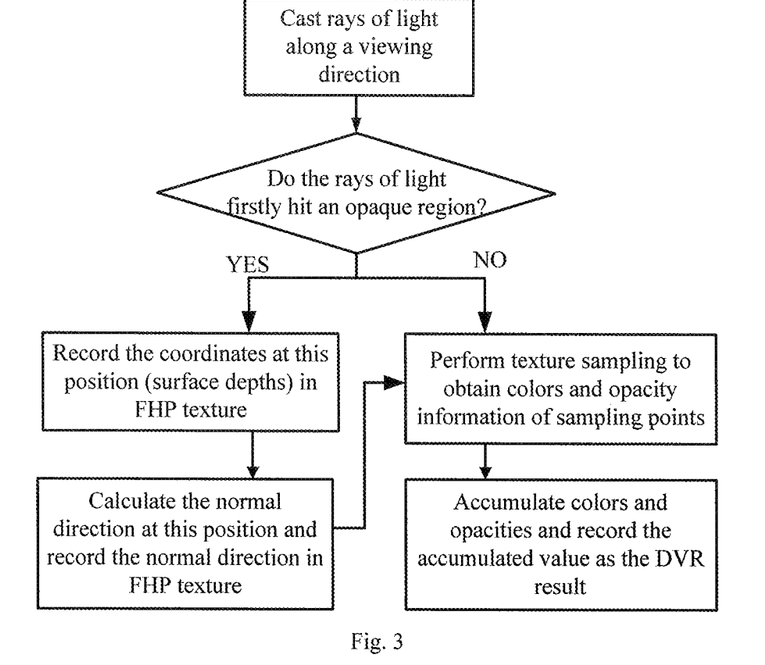
FIG. 3 is a diagram showing details of step 201 in FIG. 2.

FIG. 3 shows details of step 201. The DVR (Direct Volume Rendering) refers to searching color values and opacities of sampling points along directions of light rays using a transfer function, and obtaining color values of the pixels corresponding to a two-dimensional image by accumulation. The FHP (First Hit Position) records the position where a light ray firstly hits an opaque region in the volume data during the DVR ray casting. The FHN (First Hit Normal) refers to the normal vector at the FHP, and records the normal vector at the opaque region in the volume data which the light ray firstly hits during the casting of light rays.

Figure 4:
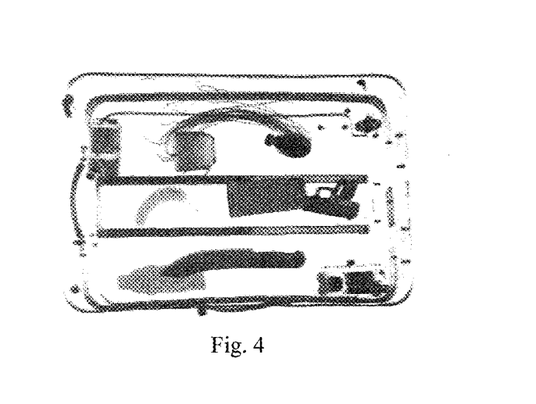
FIG. 4 is a diagram showing DVR output result according to a first embodiment of the present disclosure.

During the casting of light rays, rays are shot from a viewing point towards an imaging plane; when the rays go through the three-dimensional image, sampling is performed with a preset step length so as to obtain and accumulate color and transparency information of sampling points; finally, the direct rendering result DVR of the volume data can be obtained and outputted to the foreground for displaying, as shown in FIG. 4.

Figure 5:
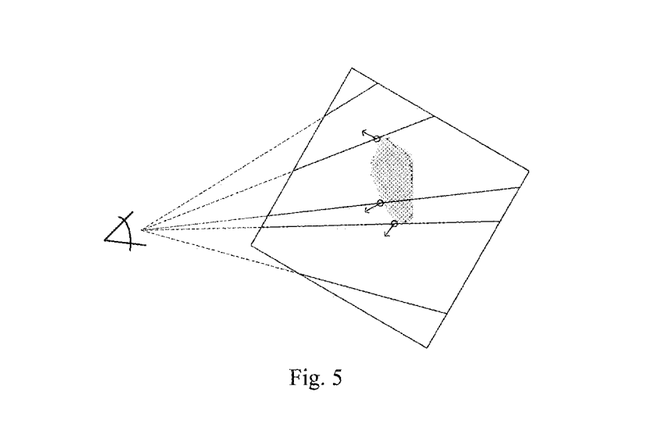
FIG. 5 is a schematic diagram illustratively showing a method for obtaining surface depth and normal direction information of an object according to a first embodiment of the present disclosure.

While color accumulation is performed, for each of the cast rays, according to a preset transparency threshold, position where the light ray firstly hit an opaque region in the CT-based image is recorded, and the position is stored in FHP texture as $(x_h, y_h, z_h)$. Meanwhile, at the voxel position, the normal vector is calculated. For example, the normal vector at the hit point is calculated using a gradient estimation at the voxel position. A gray value at $(x_h, y_h, z_h)$ is recorded as $f(x_h, y_h, z_h)$, and the gradient value is calculated and normalized using a central difference method, and then stored in the FHN texture, as shown in FIG. 5:

$$\nabla f(x_h, y_h, z_h) \approx \frac{1}{2}\begin{pmatrix} f(x_h+1, y_h, z_h) - f(x_h-1, y_h, z_h) \\ f(x_h, y_h+1, z_h) - f(x_h, y_h-1, z_h) \\ f(x_h, y_h, z_h+1) - f(x_h, y_h, z_h-1) \end{pmatrix}^{-1}$$

In step 202, a selection of an image of an object in the three-dimensional image is accepted, and a variation value of a normal direction from a starting point to an ending point of the selected object length which needs to be measured is calculated; whether the variation value is smaller than a preset angle threshold is determined; if the variation value is not smaller than a preset angle threshold, step 203 is performed; and if the variation value is smaller than a preset angle threshold, step 204 is performed.

After obtaining the starting point and the ending point of the object length which needs to be measured, based on the two-dimensional coordinates of the points in the image space, the values of the positions corresponding to the points in the FHN image can be queried. For example, the queried value of the starting point in the FHN image is denoted as $N_s$ $(x_s, y_s, z_s)$, the queried value of the ending point in the FHN image is denoted as $N_e$ $(x_e, y_e, z_e)$. Usually, users require that the starting point and the ending point of the length to be measured are on the same plane of the same object. This requirement can be met by restricting the angle variation between the normal vectors of the starting point and the ending point. For example, a variation value of vector is denoted as $\Delta N = \|N_e - N_s\|_2$; if the variation value is greater than or equal to a preset angle threshold $\varepsilon$, step 203 is performed; if the variation value is smaller than the preset angle threshold $\varepsilon$, step 204 is performed.

In step 203, a new ending point for measurement is obtained so that the variation value of the normal direction between the starting point and the new ending point for measurement is smaller than the angle threshold.

Figure 6:
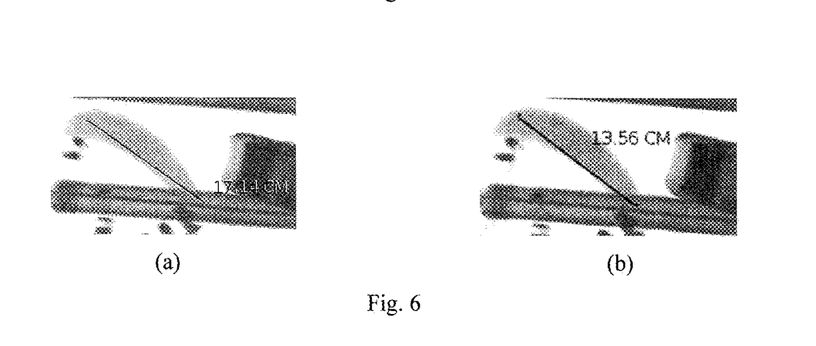

When the variation value of the normal vector is greater than or equal to the preset angle threshold $\varepsilon$, it is likely that the starting point and the ending point for measurement are not on the same object, or on different planes of the same object. For example, the queried value of the starting point in the FHP image is denoted as $P_s$ $(x_s, y_s, z_s)$, the queried value of the ending point in the FHP image is denoted as $P_e(x_e, y_e, z_e)$. Starting from the point $P_e$, a new ending point for measurement can be obtained by backtracking along the direction of $\overrightarrow{P_e P_s}$. It needs to be guaranteed that the normal vector angle variation between the starting point and the new ending point is within the angel threshold range, and then the measurement result is output in step 204. FIG. 6(a) shows the starting point and the ending point which need to be measured, and both of them are on different objects. FIG. 6(b) shows the final measurement result after processes using algorithms, as shown in the figure, the starting point and the ending point are on the same object. By such processes, the success ratio of the measurement operation can be effectively increased.

In 204, the starting point and the ending point are converted into three-dimensional coordinates according to the surface depths of the object, and the length measurement value after coordinate conversion is output.

The coordinate values of the starting point and the ending point in a physics coordinate system in the real world are denoted as $V_s$ $(x_s^v, y_s^v, z_s^v)$ and $V_e$ $(x_e^v, y_e^v, z_e^v)$, respectively, and the dimensionality value of the volume data is denoted as $(d_x, d_y, d_z)$, the pixel sizes of the volume data along individual directions are denoted as $(s_x, s_y, s_z)$; then, after the conversion into three-dimensional coordinates, the following can be obtained:

$$\begin{cases} x_s^v = x_s \times d_x \times s_x \\ y_s^v = y_s \times d_y \times s_y \\ z_s^v = z_s \times d_z \times s_z \end{cases}$$

similarly, $V_e$ $(x_e^v, y_e^v, z_e^v)$ can be obtained.

After conversion into three-dimensional coordinates, the final length measurement result is $L = \|V_e - V_s\|_2$, and the length unit is consistent with the pixel size. The pixel size refers to the physical distance between centers of two adjacent pixels in the three-dimensional rendering result.

Second Embodiment

Figure 7:
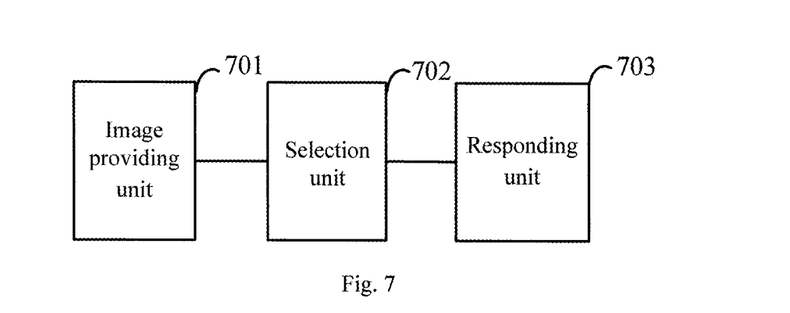
FIG. 7 is a block diagram of a device for operating a CT-based three-dimensional image used for security inspection according to a second embodiment of the present disclosure.

The second embodiment of the present disclosure provides a device for operating a CT-based three-dimensional image used for security inspection. As shown in FIG. 7, the device can include an image providing unit 701, a selection unit 702, and a responding unit 703.

The image providing unit 701 is configured to provide a CT-based three-dimensional image used for security inspection.

The selection unit 702 is configured to accept a selection to select an image of an object in the three-dimensional image provided by the image providing unit 701.

The responding unit 703 is configured to respond to the selection performed by the selection unit 702.

The device for operating a CT-based three-dimensional image used for security inspection according to the second embodiment of the present disclosure is realized based on the same idea as that of the method for operating a CT-based three-dimensional image used for security inspection.

Specifically, the selection unit 702 is configured to accept a selection to entirely select the image of the object in the three-dimensional image provided by the image providing unit 701. According to an embodiment, the selection unit 702 is configured to accept a single-click selection or a frame selection on the image of the object in the three-dimensional image to entirely select the image of the object.

Further, the selection unit 702 is configured to accept a local selection to locally select the image of the object in the three-dimensional image provided by the image providing unit 701. Specifically, the selection unit is configured to: accept a double-click selection on the image of the object in the three-dimensional image to select a section of the image of the object; or accept a local frame selection on the image of the object in the three-dimensional image to select a local region of the image of the object.

According to an embodiment, the responding unit 703 is configured to: display one or more of the following pieces of information: an image contour and a three-dimensional size of the image of the object selected by the selection unit 702, a density, an atomic number, a CT number and a substance state of the selected object, and information indicating whether the object is a hazardous object; and/or if the object selected by the selection unit 702 is a hazardous object, provide an alert or a notification.

According to an embodiment, the responding unit 703 is configured to: display one or more the following pieces of information: a size of a local region of the image of the object selected by the selection unit 702, a density, an atomic number, a CT number and a substance state of the selected object, and information indicating whether the object is a hazardous object; and/or if the object selected by the selection unit 702 is a hazardous object, providing an alert or a notification.

The embodiments of the present disclosure can have the following advantageous effects:

In the method and device for operating a CT-based three-dimensional image used for security inspection provided by the present disclosure, related information of an object image in a CT-based image can be obtained by performing selection on the CT-based image used for security inspection and responding to the selection. The present disclosure has strong practicality, and can provide effective reference information for image judgment in the CT-based security inspection field.

The modules of the device for operating a CT-based three-dimensional image used for security inspection provided by the present disclosure may be implemented with one or more digital signal processors (DSP), application specific integrated circuits (ASIC), processors, microprocessors, controllers, microcontrollers, field programmable gate arrays (FPGA), programmable logic devices, other electronic units, or any combination thereof. Some of the functions and processing described herein may also be implemented with software executed on a processor.

Certain aspects of the present disclosure may be implemented with a combination of software and hardware. For example, the method for operating the CT-based image can be performed based on program codes or instructions executed on a processor.

According to an embodiment of the present disclosure, there is provided a device for operating a CT-based three-dimensional image used for security inspection, including:
 a processor; and
 a memory for storing instructions executable by the processor;
 wherein the processor is configured to:
 provide a CT-based three-dimensional image used for security inspection;
 accept a selection to select an image of an object in the three-dimensional image; and
 respond to the selection.

Also, the above device for operating a CT-based three-dimensional image used for security inspection can further include a device for man-machine interaction, for example, an input device such as a keyboard, or a mouse.

For performing the three-dimensional measurement as mentioned in the present disclosure, the person in charge of security inspection can observe images displayed on the device, select a region of interest on the images by clicking and dragging the region using a button on the mouse (for example, pressing the button). After the button of the mouse is released, the three-dimensional measurement can be completed.

It should be noted that the above embodiments are disclosed to explain technical solutions of the present disclosure, but not for limiting purposes. While the present disclosure has been described in detail with reference to the above embodiments, one of ordinary skill in this art can understand that the technical solutions in the above embodiments can be modified, or a part of technical features can be equivalently substituted, and such modifications or substitutions will not make the essence of the technical solutions depart from the spirit or scope of the technical solutions of various embodiments in the present disclosure.

What is claimed is:

1. A method for operating a CT-based three-dimensional image used for security inspection, comprising:
 providing a CT-based three-dimensional image used for security inspection;
 accepting a selection to select an image of an object in the three-dimensional image; and
 responding to the selection;
 wherein the providing the CT-based three-dimensional image used for security inspection comprises:
  performing three-dimensional volume rendering on the CT-based image used for security inspection, and obtaining position information of surfaces of the object in the three-dimensional image;
 wherein the performing the three-dimensional volume rendering on the CT-based image used for security inspection comprises:

casting rays of light along a viewing direction,
performing volume texture sampling on the CT-based image used for security inspection according to the cast rays of light, and obtain color information, and
performing color combination and outputting a three-dimensional volume rendering result;
wherein the obtaining the position information of the surfaces of the object in the three-dimensional image comprises:
according to a preset transparency threshold, recording positions where the rays of light firstly hit opaque regions in the CT-based image used for security inspection as surface depths of the image of the object,
calculating gradient values of voxels at the positions as normal direction information of the positions, and
while outputting the three-dimensional volume rendering of the CT-based image used for security inspection, recording the surface depths and normal direction information of the image of the object in the three-dimensional image.

2. The method for operating a CT-based three-dimensional image used for security inspection according to claim 1, wherein the accepting the selection to select the image of the object in the three-dimensional image, comprises:
accepting a selection to entirely select the image of the object in the three-dimensional image.

3. The method for operating a CT-based three-dimensional image used for security inspection according to claim 2, wherein the accepting the selection to entirely select the image of the object in the three-dimensional image, comprises:
accepting a single-click selection or a frame selection on the image of the object in the three-dimensional image to entirely select the image of the object.

4. The method for operating a CT-based three-dimensional image used for security inspection according to claim 1, wherein the accepting the selection to select the image of the object in the three-dimensional image, comprises:
accepting a local selection to locally select the image of the object in the three-dimensional image.

5. The method for operating a CT-based three-dimensional image used for security inspection according to claim 4, wherein the accepting the local selection to locally select the image of the object in the three-dimensional image comprises:
accepting a double-click selection on the image of the object in the three-dimensional image to select a section of the image of the object; or
accepting a local frame selection on the image of the object in the three-dimensional image to select a local region of the image of the object.

6. The method for operating a CT-based three-dimensional image used for security inspection according to claim 2, wherein the responding to the selection comprises;
displaying one or more of the following pieces of information: an image contour and a three-dimensional size of the image of the selected object, a density, an atomic number, a CT number and a substance state of the selected object, and information indicating whether the object is a hazardous object; and/or
if the object is a hazardous object, providing an alert or a notification.

7. The method for operating a CT-based three-dimensional image used for security inspection according to claim 4, wherein the responding to the selection comprises:
displaying one or more the following pieces of information; a size of a local region of the image of the selected object, a density, an atomic number, a CT number and a substance state of the selected object, and information indicating whether the object is a hazardous object; and/or
if the object is the hazardous object, providing an alert or a notification.

8. The method for operating a CT-based three-dimensional image used for security inspection according to claim 1, wherein the responding to the selection comprises:
obtaining size information of the selected part according to the surface depths and the normal direction information;
wherein the obtaining of the size information comprises:
calculating a variation value of a normal direction from a starting point to an ending point of the selected part; if the variation value is smaller than a preset angle threshold, querying the surface depths and converting the starting point and the ending point into three-dimensional coordinates, and outputting size measurement values in directions in which measurements are needed after coordinate conversion.

9. The method for operating a CT-based three-dimensional image used for security inspection according to claim 1, wherein the responding to the selection comprises:
obtaining voxel collections for different objects in the CT-based three-dimensional image used for security inspection by dividing;
determining at least one selected object from the voxel collections for different objects based on different preset criteria; and
performing statistics on voxel information corresponding to the at least one selected object, and outputting size measurements of the object in a three-dimensional space.

10. A device for operating a CT-based three-dimensional image used for security inspection, comprising:
a processor; and
a memory for storing instructions executable by the processor;
wherein the processor is configured to:
provide a CT-based three-dimensional image used for security inspection;
accept a selection to select an image of an object in the three-dimensional image; and
respond to the selection:
wherein the providing the CT-based three-dimensional image used for security inspection comprises:
performing three-dimensional volume rendering on the CT-based image used for security inspection, and
obtaining position information of surfaces of the object in the three-dimensional image;
wherein the performing the three-dimensional volume rendering on the CT-based image used for security inspection comprises:
casting rays of light along a viewing direction,
performing a volume texture sampling on the CT-based image used for security inspection according to the cast rays of light, and obtain color information, and
performing color combination and outputting a three-dimensional volume rendering result;
wherein the obtaining the position information of the surfaces of the object in the three-dimensional image comprises:
according to a preset transparency threshold, recording positions where the rays of light firstly hit opaque regions in the CT-based image used for security inspection as surface depths of the image of the object, calculating gradient values of voxels at the positions as normal direction information of the positions, and while outputting the three-dimensional volume rendering of the CT-based image used for security inspection, recording the surface depths and normal direction information of the image of the object in the three-dimensional image.

11. The device according to claim 10, wherein the processor is configured to accept a selection to entirely select the image of the object in the three-dimensional image.

12. The device according to claim 11, wherein the processor is configured to accept a single- click selection or a frame selection on the image of the object in the three-dimensional image to entirely select the image of the object.

13. The device according to claim 10, wherein the processor is configured to accept a local selection to locally select the image of the object in the three-dimensional image.

14. The device according to claim 13, wherein the processor is configured to:

accept a double-click selection on the image of the object in the three-dimensional image to select a section of the image of the object; or accept a local frame selection on the image of the object in the three-dimensional image to select a local region of the image of the object.

15. The device according to claim 11, wherein the processor is configured to:

display one or more of the following pieces of information: an image contour and a three-dimensional size of the image of the selected object, a density, an atomic number, a CT number and a substance state of the selected object, and information indicating whether the object is a hazardous object; and/or if the object is a hazardous object, provide an alert or a notification.

16. The device according to claim 13, wherein the processor is configured to:

display one or more the following pieces of information: a size of a local region of the image of the selected object, a density, an atomic number, a CT number and a substance state of the selected object, and information indicating whether the object is a hazardous object; and/or if the object is the hazardous object, provide an alert or a notification.

* * * * *